(12) United States Patent
Benemann et al.

(10) Patent No.: US 7,575,907 B1
(45) Date of Patent: Aug. 18, 2009

(54) PROCESS FOR MICROBIAL PRODUCTION OF HYDROGEN AND METHANE FUELS

(76) Inventors: John Rudiger Benemann, 3434 Tice Creek Dr., #1, Walnut Creek, CA (US) 94595; Don Churchill Augenstein, 4277 Pomona Ave., Palo Alto, CA (US) 94306

( * ) Notice: Subject to any disclaimer, the term of this patent is extended or adjusted under 35 U.S.C. 154(b) by 394 days.

(21) Appl. No.: 11/035,868

(22) Filed: Jan. 10, 2005

Related U.S. Application Data

(60) Provisional application No. 60/535,592, filed on Jan. 8, 2004.

(51) Int. Cl.
*C12P 5/02* (2006.01)
*C12P 3/00* (2006.01)

(52) U.S. Cl. .................... 435/167; 435/168
(58) Field of Classification Search ............. 435/167, 435/168
See application file for complete search history.

(56) References Cited

U.S. PATENT DOCUMENTS

| | | | |
|---|---|---|---|
| 4,480,035 A | | 10/1984 | Roychowdhury |
| 4,696,746 A | * | 9/1987 | Ghosh et al. ............... 210/603 |
| 4,921,800 A | | 5/1990 | Vatsala |
| 5,350,685 A | | 9/1994 | Taguchi et al. |
| 5,464,539 A | | 11/1995 | Ueno et al. |
| 5,500,123 A | * | 3/1996 | Srivastava ................. 210/603 |
| 5,705,374 A | | 1/1998 | Sanford et al. |
| 5,804,424 A | | 9/1998 | Kaplan et al. |
| 5,834,264 A | | 11/1998 | Sanford et al. |
| 6,342,378 B1 | * | 1/2002 | Zhang et al. .............. 435/168 |
| 6,569,332 B2 | * | 5/2003 | Ainsworth et al. .......... 210/603 |

FOREIGN PATENT DOCUMENTS

DE  3427976  *  4/1985

OTHER PUBLICATIONS

Benemann, J. 1996. Hydrogen biotechnology: progress and prospects. Nature *Biotechnology* 14:1101-1103.
Hallenbeck, P.C., J.R. Benemann. 2002. Biological hydrogen production; fundamentals and limiting processes. *Int. J. Hydrogen Energy* 27:1185-1193.
Cooney, M. N. Maynard, C. Cannizzaro, and J. Benemann (2007) Two-phase anaerobic digestion for production of hydrogen-methane mixtures. 98:2641-2651.
Prescott, L.M., J.P. Harley, and D.A. Klein. (1996) Microbiology, Third Edition. Wm. C. Brown Publishers, Dubuque, Iowa., pp. 482-485 and 843-846.

* cited by examiner

*Primary Examiner*—Herbert J. Lilling
(74) *Attorney, Agent, or Firm*—Hugh McTavish

(57) ABSTRACT

The invention provides a process for producing hydrogen and methane gases by microbial fermentation. The process involves a first reactor in which a fermentation produces hydrogen and a liquid effluent. The liquid effluent is fermented in a second reactor to produce methane. The ratio of hydrogen to methane produced is adjusted by adjusting the liquid volume of the first reactor.

6 Claims, 1 Drawing Sheet

PROCESS FOR MICROBIAL PRODUCTION OF HYDROGEN AND METHANE FUELS

This application claims priority under 35 U.S.C. § 120 to U.S. provisional patent application Ser. No. 60/535,592, titled Process for Microbial Production of Hydrogen and Methane Fuels, filed Jan. 8, 2004.

FIELD OF INVENTION

This invention relates to a process for the biological production of hydrogen and methane gases by microbial fermentation.

BACKGROUND

The production of methane gas by microbial fermentations is a well-established technology with many commercial applications in waste treatment and biomass conversion for over 100 years. By contrast, hydrogen ($H_2$) fermentations—that is, the anaerobic conversion of organic substrates to $H_2$ gas—have not been developed to practical applications despite a great deal of research (reviewed in Hallenbeck and Benemann, 2002; see Literature Cited) and many patents (see Patents Listed) covering various methods of $H_2$ fuel production by fermentations. One major reason for this relative lack of success is that the yield of $H_2$ has been rather low, generally less than 20% on an energy (fuel) content basis compared to the yield of methane or ethanol fermentations under similar conditions. That has discouraged practical applications.

An extensive literature exists on two-stage, also called "two-phase", methane fermentations, which produce $H_2$ gas in the first stage (or phase) and methane gas in the second stage. However, the prior art does not disclose the harvesting of both $H_2$ and $CH_4$ or of $H_2$—$CH_4$ mixtures in an integrated process. Indeed, in most of the descriptions in the literature, no mention is made of the nature of the gas produced in the first stage, which is often not even analyzed. Furthermore, often the gas from the first phase is transferred into the second, to allow any $H_2$ produced in the first stage to be converted to methane gas in the second, which is the only fuel produced by such anaerobic digestion systems.

In certain applications the production of $H_2$—$CH_4$ mixtures could be of interest, in particular due to the reduction in $NO_x$ and other pollutants that result from the combustion of such mixtures in engines, compared to $CH_4$ combustion alone. Thus combustion of such $H_2$—$CH_4$ mixtures is of interest in use of biogas for electricity generation or transportation applications wherever air pollution is an issue. Thus, it has been proposed that two-stage fermentations that produce both $H_2$ and $CH_4$ could be also used to produce such $H_2$—$CH_4$ mixtures for air pollution reduction (in particular $NO_x$ reduction) purposes (Benemann, 1996, 1998). However, for practical applications methods must be developed to allow for control over the relative volumes of these two gases such that the combined gas composition can be maintained at a desired level for the application at hand, even when the fermentation substrate (feed), changes in nature or flow, or both, or when other performance parameters in the reactor, such as acidity, temperature, gas flow, or composition, change, resulting in reduced or excessive $H_2$ production. For many applications it would be desirable to produce $H_2$ gas at or near the maximum amount that is feasible by such fermentation processes, with or without admixture of the $CH_4$ gas produced in the second stage. This objective requires optimization of the operating conditions, in particular of the hydraulic retention time and loading rate as well as of the $H_2$ concentration, and other performance parameters in the first stage of the process. A process for accomplishing these objectives is described herein.

SUMMARY

The invention provides a process for the production of a mixture of gases containing $H_2$ and $CH_4$ by microbial fermentation of fermentable materials such as sugars, starches, celluloses, and other biological materials. The process involves a two stage fermentation process, in which the liquid volume of the first stage is varied in proportion to the volume of the second stage and in which the methane-containing gas from the second stage is directed into the first stage, such that the amount of $H_2$ gas produced in the first stage can be maximized or optimized to provide the proportion of the two gases desired for the particular application at hand. For a given feed—that is, fermentation feed flow and composition—the production of $H_2$ gas in the first stage is determined mainly by the hydraulic dilution rate and by the partial pressure of the $H_2$ gas in solution, both of which are controlled in the disclosed process. The first is controlled by changing the working volume of the first stage bioreactor, and the second by directing a portion or all of the biogas ($CH_4$ and $CO_2$) produced in the second stage through the first stage, thus lowering the liquid side $H_2$ concentration. Using these methods in conjunction or singly allows adjustment of the composition and relative $H_2$ and $CH_4$ gas volumes produced, either as separate gas streams of $H_2$ and $CH_4$ or as mixtures of the two gases, in either case ranging on a relative volumetric basis from 0.1:1 to 1:1.

DETAILED DESCRIPTION

Figure 1:
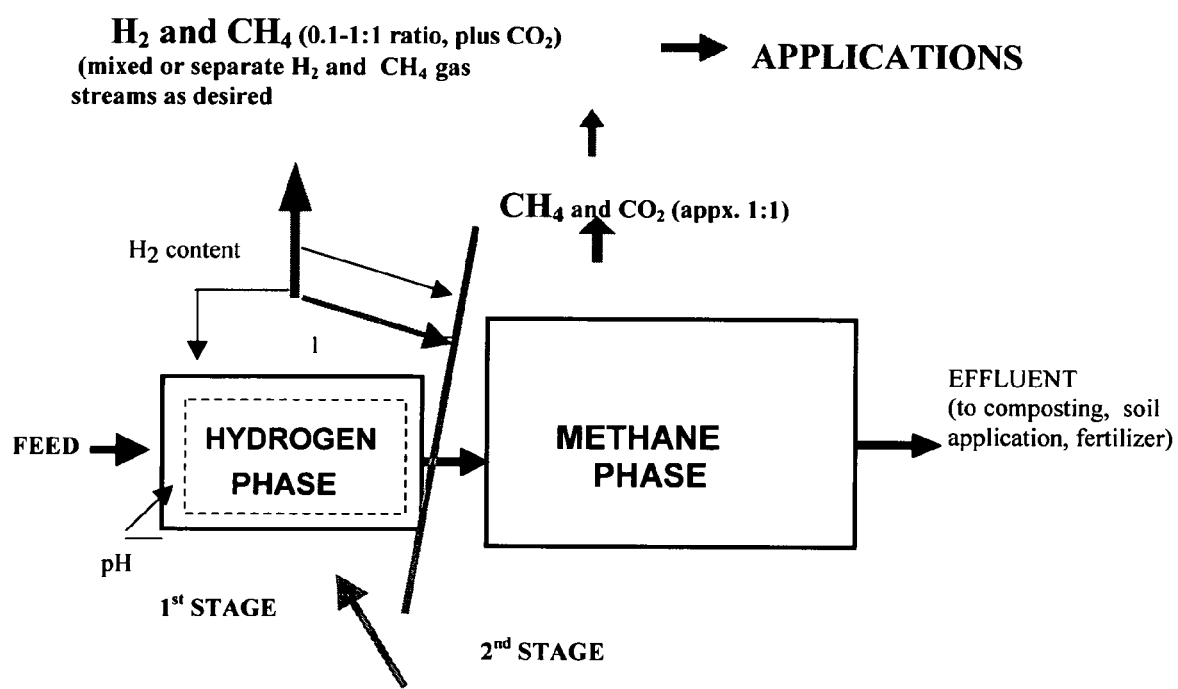
FIG. 1 is a schematic representation of a process for producing hydrogen and methane.

The major factor limiting $H_2$ production by microbial fermentations is the thermodynamics of such processes, which reduce the achievable yields with conventional anaerobic $H_2$ fermentations to a maximum of about one-third, on a fuel energy content basis, compared to what can be and is achieved with other fuel-producing anaerobic fermentations, specifically methane fermentations, also known as anaerobic digestion, and ethanol fermentations. Even a one-third yield is seldom observed, and then only under extreme and impractical conditions, with more typical yields in the one-tenth to one-fifth range, again compared to methane or ethanol energy yields from the same substrates. Actual $H_2$ yields depend on several factors, including, among others, the microbial population present, the conditions of the fermentation process (in particular the hydrogen ion concentration, that is pH, of the broth), the temperature of the process, the mixing in the reactor, the $H_2$ concentration dissolved in the liquid phase, and, perhaps most importantly, the nature of the substrates being fermented, with sugars, and polymers from which these can be derived (starches, glycogen, cellulose or pre-treated lignocellulosics, for main examples) being the main substrates for the $H_2$ produced by such bacterial fermentations.

The operating conditions of the two-stage (two-phase) bioreactor (fermenter) process must be controlled in response to changes in fermentation feed and other variables (temperature, pH, $H_2$ concentrations, and fatty acids, among others) so as to maximize $H_2$ production in the first stage or, if a specific mixed gas composition is desired, to adjust the relative amounts of $H_2$ and $CH_4$ produced in each of the two stages.

Mixed gases can be obtained by simply blending the $H_2$ with $CH_4$ after these are produced separately by the two stages, but such an approach does not allow any process control to achieve gas yield or composition objectives. This invention addresses the requirements for maximal $H_2$ production and/or desired $H_2:CH_4$ mixtures through a novel process control method that incorporates two features that allow for such regulation: First, the working volume for the first stage of the reactor is varied, with the second stage at near constant liquid volume, to dynamically accommodate the bacterial population simultaneously to changes in the performance of the bioreactor system, as well as changes in the flows and composition of the incoming feed. Second, biogas from the second stage is circulated through the first stage to reduce the partial pressure of $H_2$ in the first stage and thus increase the total amount and rate of $H_2$ produced. This results in a maximal amount of a desired mixture of the two fuels. These two feedback control methods—operating a two-stage system with the first stage of variable and the second of essentially fixed volume, and sparging the liquid of the first stage with gas produced by the second phase—maximize overall gas production with a minimum of overall size of the bioreactor system, and can be adapted for the specific feedstock and other process requirements, tailored to the particular local operating regimes and process applications. The feedback processes can be operated independently or in unison. They can be operated either manually, based on a minimum of experience, theory, models and process data, such as knowledge of optimum pH and control strategies, or automatically, based on more sophisticated process information and application of well known control algorithms.

For a given feed (substrate), such as molasses, starches, other metabolizeable organic substrates, including waste materials containing a high proportion of such fermentable substrates, the hydraulic dilution rate (flow per unit volume) and loading rate (amount of substrate per unit volume per unit time) in the first stage are the parameters that can be most easily adjusted to control and maximize $H_2$ yields, although other control parameters are and can be used in conjunction with these, such as pH control by base addition, mixing by recirculation (liquid or gas) or mechanical means, and temperature control, with the two stages operated at the same or different temperatures. Although these latter process controls are widely studied and practiced, a combined volume and hydraulic flow adjustments for the first stage in such a process is not practiced or described in the literature and neither is gas recirculation from the second to the first reactor. These control factors also greatly reducing the need for pH management or mechanical or gas recirculation mixing alone. However, such volume-flow adjustments are generally not reported for two-phase (or two-stage) fermentations, and if adjustments are made these are not with the objective of increasing $H_2$ yields or relative fuel composition of the two stages, but rather for maximizing methane production or more effectively destroying infectious agents and parasites in the overall system. Furthermore, such adjustments are generally made by simply changing flow rates (e.g., hydraulic dilution rate) of the feed entering the first stage, which is not generally practical where feed flows are fixed or where variable amounts of substrates are present (e.g., waste treatment processes).

In the present invention the first control variable is the working volume of the first reactor. Since changing the volume at fixed flow-rate and composition, changes inversely both hydraulic retention time and loading rate, first-stage volume changes incorporates both hydraulic retention time and loading rate into one control parameter. In brief, this invention incorporates a feedback controlled operation of the first stage in which the liquid volume of the first stage is much smaller, some 5 to 50 times smaller, than that of the second stage (usually the first stage will be operated in a volume range of 8 to 40 times smaller than the second stage). The difference in hydraulic retention time between the two vessels is proportional to the difference in volume, so if the first vessel is 40 times smaller than the second vessel, the hydraulic retention time in the first vessel is also 40 times less than in the second vessel. The capacity of the first vessel is determined by the maximum volume in relation to the second vessel that will be needed. As noted, the volume of the first vessel can be as large as 5 times smaller than the second vessel. So the capacity of the first vessel can be 5 times smaller than the second. The first vessel is operated at less than full capacity volume when the ratio of volumes is to be altered. Thus, if a ratio of volumes of 1 to 50 is desired, the first vessel is operated with a liquid volume of 10% of capacity.

Relatively small changes in the overall retention time can accommodate even larger variations in the relative volume and hydraulic retention times in the first reactor. As methane fermentations are the slower of these two processes, these dictate the overall necessary hydraulic retention time, and a second stage which is much larger than that of the first stage, in particular where larger particle sizes and low biodegradablilty limit the rate of enzymatic breakdown of the substrates. The liquid volume in the first stage is adjusted over a relatively large range in response to incoming feed flow or composition variations or variations in first stage operating parameters, such as pH and gas compositions (e.g. $H_2$ gas concentrations) and rates. It can also be adjusted in response to second stage variables. The adjustment of the first-stage liquid volume allows control over gas composition and production rate, with maximization if desired of $H_2$ yields, while leaving the second larger bioreactor stage at much more and generally nearly constant working volume.

Factors that require an increase in the first stage hydraulic retention time, and thus volume (at constant flow), are increasing base consumption for pH control or a pH decline, decline in $H_2$ concentration in the biogas produced, and decline in rate of $H_2$ production, among others. Factors that allow a reduction in retention time and volume in the first stage are the converse, that is pH increases and stable $H_2$ production. Those versed in the art will be able to apply appropriate algorithms to allow for automatic control over the process.

Thus, for the present invention, the first stage would be designed to accommodate a working volume that is within the range of the expected volume variations for the specific feed and application desired. Achieving a change in dilution and loading rates in the first stage by controlling the working volume of the first bioreactor can be based on various methods, including the following: varying the height of an overflow pipe, for bioreactors situated above the height of the second stage liquid level; increasing the gas pressure in the first stage to force overflow into the second stage for when the first reactor liquid level has a lower elevation than the second reactor; using pumps with level controllers in the first stage; using inflation devices in the first stage to reduce its working volume; using movable baffles; using multiple siphons; or using other such methods as are known in the art and may be applicable to specific circumstances under consideration.

These adjustments in first stage reactor working volume are be controlled primarily by the pH and gas flow and composition in the first stage. A pH optimum for maximal gas production can be quickly established for each individual waste and can serve as a primary indicator for optimizing reaction volume for a given influent flow and composition. Operation at a pH level below 6 is a desirable adjunct to the first stage process since such pH levels tend to limit the growth of methane producing bacteria in the first stage, which might otherwise limit or even prevent $H_2$ evolution in this stage. Inputs for feedback control for the maximal or optimal gas production in the first stage can also include additional parameters, such as gas production rates and composition, volatile acids, and other data that allow for additional and better optimized control.

It should be recognized that the second stage is of a fixed volume and that there is no advantage to changing the working volume of the second stage, as would be apparent and known to those versed in the art of anaerobic digestion and methane production. The second stage volume determines the amount of methane produced, and one would always want to maximize the amount of methane produced, while adjusting the amount of $H_2$ produced relative to methane. Thus, the second stage vessel liquid volume is substantially fixed.

Adjustment of hydraulic dilution rate by changing the working volume of the first stage in response to changing substrate composition or even changing flow can provide maximal $H_2$ yields in the first stage if $H_2$ is desired to be kept free of methane. This is a sufficient tool where $H_2$ is to be used separately from methane gas. If defined mixtures of $H_2$ and $CH_4$ are desired for particular applications, these could be generated by mixing the separate gas streams produced by the two stage bioreactors. However, it is more advantageous and results in higher $H_2$ yields, a major objective of $H_2$ fermentations, if the gas from the second, $CH_4$-producing, stage is transferred through the first stage. The $CH_4$ gas causes a reduction in the partial pressure of $H_2$, thereby resulting in an increase in $H_2$ yields. Thus, this method increases total $H_2$ production and $H_2$ concentrations in the mixed $H_2$/$CH_4$ mixtures well above what would be possible with mixing the gaseous products of the two stages separately. The ratio of $H_2$:$CH_4$ in the product gas can be adjusted by control of the amount of gas circulation between the second stage and the first, along with by feedback control over the liquid volume of the first stage, as described previously. This allows for dynamic and effective control over the relative amounts of $H_2$ and $CH_4$ produced by these fermentations. The range in relative gas composition achievable is 1:10 to 1:1 $H_2$:$CH_4$. The ratio can be varied based on specific needs and requirements.

Other gases, in particular $CO_2$, water vapor, and $H_2S$, are also present but do not affect the overall process. $CO_2$ concentrations can, however, be used as indication of process status, in particular in the first stage, with elevated concentration of $CO_2$ indicating the process is not working optimally. As stated above, other control methods can also be added in combination with the two above, such as increasing or decreasing the amount of mixing (by mechanical means or by, e.g., gas recirculation, see 1 in the Schematic below), varying the temperature (higher temperatures generally favor $H_2$ production), the use of selected bacterial cultures, including genetically modified organisms, and varying nutrient levels, base, or even acid, by additions as required, etc. Such variations would be apparent to those versed in the art of anaerobic digestion and bacterial fermentations and do not fundamentally affect the nature or application of the present invention.

FIG. 1 shows some of the key control parameters available and claimed under this invention, including a feedback from the reactor operating conditions, in particular pH and also volatile acids, to adjust the working liquid volume of the first reactor, along with feedback from gas output to regulate the amount of retention time and corresponding $H_2$ level.

Black thick arrows in FIG. 1 indicate liquid flows; gray thick arrows indicate gas flows (gray line 1 is an internal gas circulation in the 15' Stage for mixing); and thin arrows indicate feedback control loops. FIG. 1 shows the $1^{st}$ stage bioreactor liquid volume is adjusted (as represented by solid and dashed lines) based on feedback control based on first stage bioreactor pH and $H_2$ content. FIG. 1 also shows that the second stage gas output flow through the first stage is adjusted based on $H_2$ content of the first stage gas output. Additional feedback loops can be established, including from incoming feed and from the 2nd stage to the 1st stage, as well as other process parameters.

LITERATURE CITED

Hallenbeck, P. C. and J. R. Benemann "Biological Hydrogen Production; Fundamentals and Limiting Processes" *Intl. J. Hydrogen Energy*, in press, 2002

Benemann, J. R., "The Technology of Biohydrogen", In *Biohydrogen*, O. Labors et al., eds., Plenum Press, New York pp. 19-30 (1998).

Benemann, J. R., "Hydrogen Biotechnology: Progress and Prospects". *Nature Biotechnology*, 14: 1101-1103 (1996).

PATENTS LISTED

Kaplan, S., and M. D. Moore, "Process for the production of hydrogen using photosynthetic proteobacteria", U.S. Pat. No. 5,804,424 (1998).

Roychowdhury, S., "Production of hydrogen", U.S. Pat. No. 4,480,035 (1984).

Sanford, R. A., J. M. Tiedje, J. A. Breznak, and J. W. Urbance, Process for anaerobic production of hydrogen using a delta-proteobacterium. U.S. Pat. Nos. 5,834,264 and 5,705,374 (1998).

Taguchi, F., M. Morimoto, T. Kyoya, and M. Takano, "Microorganisms useful for hydrogen gas production". U.S. Pat. No. 5,350,692, and "Process for preparing hydrogen gas using microorganism". U.S. Pat. No. 5,350,685 (1994).

Ueno, Y., M. Morimoto, S. Ootsuka, T. Kawai, and S. Satou, "Process for the production of hydrogen by microorganisms" U.S. Pat. No. 5,464,539 (1995).

Vatsala, T. M. "Microbial process for photohydrogen production from cellulose in high saline water medium". U.S. Pat. No. 4,921,800 (1990).

All patents, patent documents, and references cited are incorporated by reference.

What is claimed is:

1. A process for producing a gas comprising $H_2$ and a gas comprising $CH_4$, the process comprising:
    microbially fermenting a substrate in a liquid volume in a first reactor to produce a gas comprising $H_2$ and an effluent; and
    microbially fermenting the effluent of the first reactor in a liquid volume of a second reactor to produce a gas comprising $CH_4$;
    wherein the ratio of $H_2$ produced in the first reactor to $CH_4$ produced in the second reactor is adjusted by adjusting the liquid volume of the first reactor, while keeping the liquid volume of the second reactor substantially constant;
    wherein at least a portion of the gas produced in the second reactor is recirculated through the first reactor to increase the amount of $H_2$ produced in the first reactor over the amount of $H_2$ produced in the absence of gas recirculation.

2. The process of claim 1 wherein the liquid volume of the first reactor is adjusted based on pH of the first-reactor liquid, gas flow rate from the first reactor, and/or composition of the first-reactor gas.

3. The process of claim 1 wherein the ratio of $H_2$ to $CH_4$ produced is adjusted by adjusting the flow rate of gas from the second reactor into the first reactor in the recirculation.

4. The process of claim 1 or 3 wherein the ratio of $H_2$ produced to $CH_4$ produced is in the range of 0.1:1 to 1:1.

5. The process of claim 1 wherein the substrate is added to the first reactor as an influent feed, wherein the first-reactor liquid volume and/or the flow rate of gas from the second reactor into the first reactor are adjusted in response to volume, flow rate, pH, and/or composition of the influent feed to alter the ratio of $H_2$ and $CH_4$ produced by the two reactors.

6. The process of claim 1 wherein the production of $H_2$ gas in the first-reactor gas is adjusted by adjusting mechanical mixing of the first reactor, gas recirculation mixing of the first reactor, temperature, pH, or by the use of one or more selected microorganisms.

* * * * *